United States Patent [19]

Medwid et al.

[11] Patent Number: 4,829,089
[45] Date of Patent: May 9, 1989

[54] SUBSTITUTED PIPERAZINE-1,4-NAPHTHALENEDIONES USEFUL AS ANTI-ASTHMATIC AGENTS

[75] Inventors: Jeffrey B. Medwid, West Nyack; Lawrence W. Torley, Washingtonville, both of N.Y.; Andrew S. Tomcufcik, Old Tappan, N.J.

[73] Assignee: American Cyanamid Company, Stamford, Conn.

[21] Appl. No.: 222,989

[22] Filed: Jul. 22, 1988

Related U.S. Application Data

[62] Division of Ser. No. 46,365, May 6, 1987, Pat. No. 4,771,061, which is a division of Ser. No. 811,122, Dec. 19, 1985, Pat. No. 4,686,220.

[51] Int. Cl.$^4$ .................... A61K 31/135; C07C 95/08; C07C 87/28
[52] U.S. Cl. .................... 514/649; 514/476; 514/481; 514/482; 514/485; 514/590; 514/608; 514/617; 514/630; 514/657; 564/32; 564/204; 564/212; 564/220; 564/341; 564/342; 564/369; 564/370; 564/428
[58] Field of Search ................. 564/32, 204, 212, 220, 564/341, 342, 369, 370, 428, 123; 514/476, 481, 482, 485, 590, 617, 630, 608, 649, 657

[56] References Cited

PUBLICATIONS

Bell et al., Annual Reports in Medicinal Chem. 14, 51 (1979).
Lichtenstein et al., J. Exp. Med. 120, 507–530 (1984).

Primary Examiner—Donald G. Daus
Assistant Examiner—Cecilia Shen
Attorney, Agent, or Firm—Edward A. Conroy, Jr.; Robert P. Raymond

[57] ABSTRACT

This disclosure describes certain substituted piperazine-1,4-naphthalenediones useful as anti-asthmatic agents.

6 Claims, No Drawings

SUBSTITUTED PIPERAZINE-1,4-NAPHTHALENEDIONES USEFUL AS ANTI-ASTHMATIC AGENTS

CROSS REFERENCE TO RELATED APPLICATION

This application is a division of our copending application Ser. No. 046,365, filed May 6, 1987, now U.S. Pat. No. 4,771,061 which is a division of our application Ser. No. 811,122, filed Dec. 19, 1985, now U.S. Pat. No. 4,686,220.

SUMMARY OF THE INVENTION

This invention is concerned with new compounds selected from those of the formula:

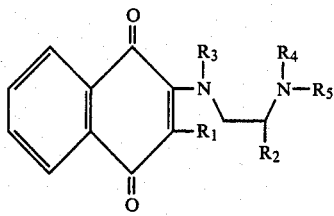

wherein $R_1$ is selected from the group consisting of halogen, hydroxy, alkyl($C_1$-$C_4$), alkoxy($C_1$-$C_3$), —NHCOCH$_3$ and —N(COCH$_3$)$_2$; $R_2$ is selected from the group consisting of hydrogen and alkyl($C_1$-$C_4$); $R_3$ and $R_4$ are individually alkyl($C_1$-$C_3$), or when taken together are —(CH$_2$)$_n$—, where n is an integer 2 or 3; $R_5$ is selected from the group consisting of hydrogen, formyl, acetyl, —COOalkyl($C_1$-$C_4$), —COOCH$_2$C—(halogen)$_3$, —CO(CH$_2$)$_7$CH=CH(CH$_2$)$_7$CH$_3$, —CON[alkyl($C_1$-$C_3$)]$_2$, phenyl, benzyl, 2-, 3- or 4-pyridinyl, 2-pyrimidinyl, 2-, 3- or 4-halobenzoyl, 2-, 3- or 4-alkyl($C_1$14 $C_6$)benzoyl, monosubstituted phenyl (wherein the substituents may be ortho, meta or para and are selected from the group consisting of halogen and trifluoromethyl), monosubstituted phenyl carboxamide (wherein the substitutents may be meta and para and are selected from the group consisting of halogen and trifluoromethyl),

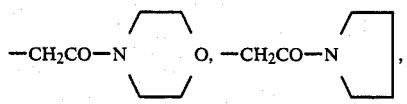

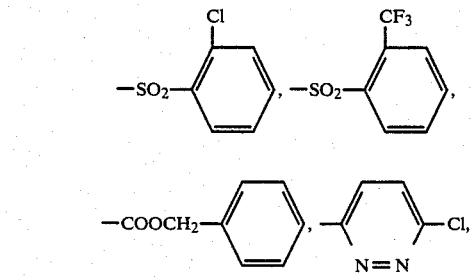

-continued

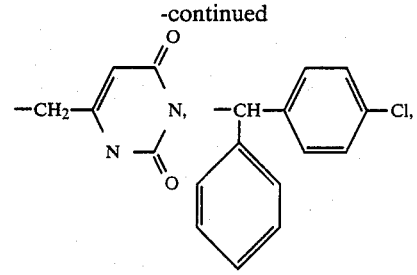

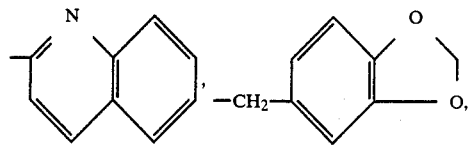

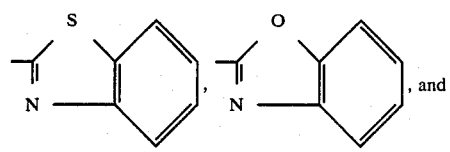

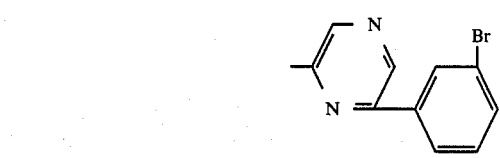

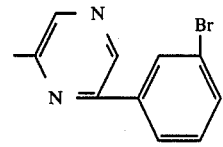

the pharmacologically acceptable acid-addition salts thereof.

In addition this invention is concerned with a method of treating asthma and allergic diseases and inflammation in warm-blooded animals and with compositions of matter employing the above compounds.

Further, this invention is concerned with processes of producing the above compounds.

DESCRIPTION OF THE INVENTION

The compounds of this invention may be prepared by the following methods:

FLOWCHART I

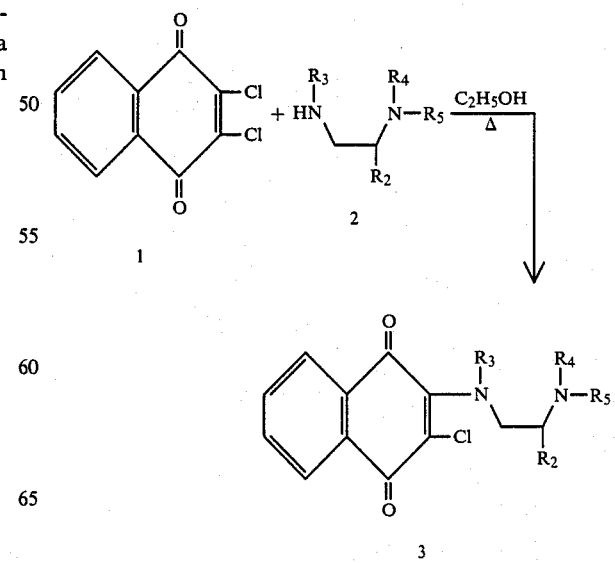

According to Flowchart I, 2, 3-dichloronaphthoquinone 1, is reacted with an amine 2, where $R_2$, $R_3$, $R_4$ and $R_5$ are as described above, in absolute ethanol at reflux for several hours producing the 3-chloro-1,4-napththa-lenedione derivatives 3.

FLOWCHART II

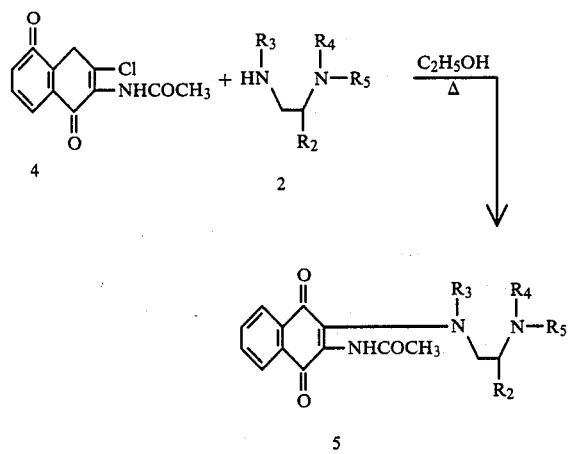

According to Flowchart II, substituting 2-acetylamino-3-chloro-1,4-naphthoquinone 4 in the reaction described for Flowchart I produces the 3-acetylamino-1,4-naphthalenedione derivatives 5.

FLOWCHART III

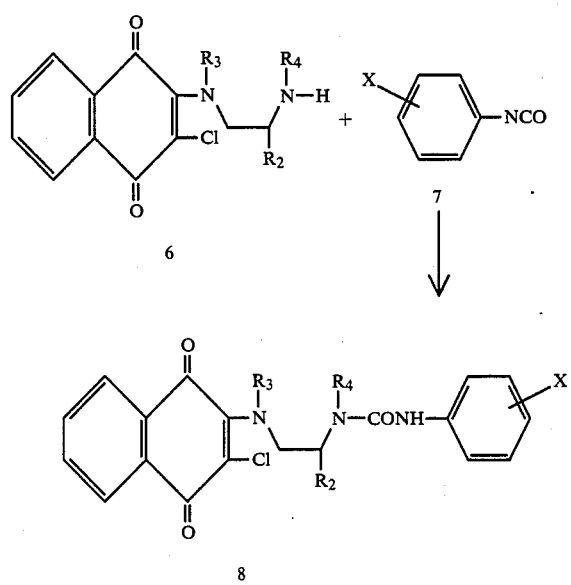

According to Flowchart III, a 3-chloro-2-substituted-1,4-naphthalenedione 6, where $R_2$, $R_3$ and $R_4$ are as described above is reacted with a substituted phenyl isocyanate 7, where X is halogen or trifluoromethyl in an organic solvent such as chloroform or ether for several hours, producing the 3-chloro-1-piperazinecarboxamide derivatives 8.

FLOWCHART IV

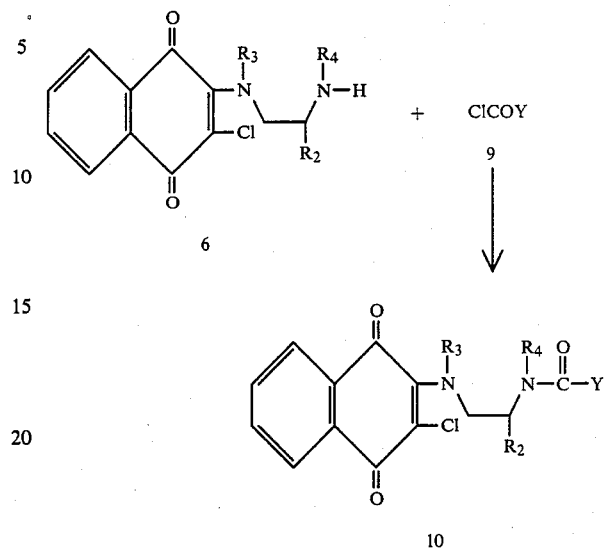

According to Flowchart IV, a 3-chloro-2-substituted-1,4-naphthalenedione 6, where $R_2$, $R_3$ and $R_4$ are as described above is reacted with a carbonyl chloride 9, where Y may be O-alkyl($C_1$–$C_6$), dimethylamino, substituted phenyl [wherein the substituents may be halogen or alkyl-($C_1$–$C_4$)], O-benzyl, —$OCH_2C$(halogen)$_3$ or —$(CH_2)_7CH=CH(CH_2)_7CH_3$ in tetrahydrofuran producing the 3-chloro-1,4-naphthalenedione carboxylic acid derivatives 10.

FLOWCHART V

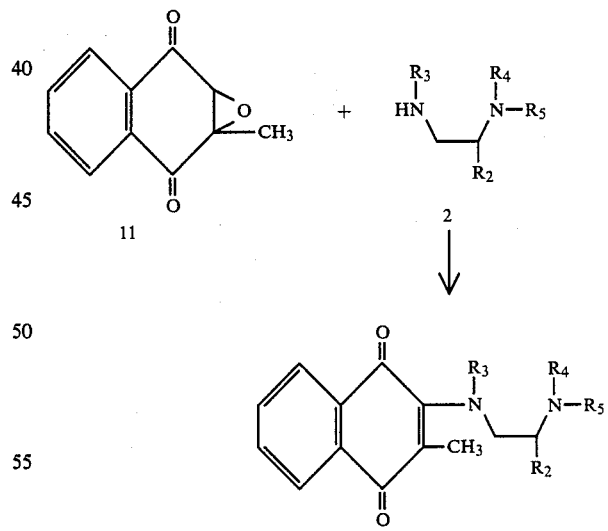

According to Flowchart V, 2,3-epoxy-2-methyl-1,4-naphthoquinone 11 is reacted with an amine 2, where $R_2$, $R_3$, $R_4$ and $R_5$ are as described above, in absolute ethanol with heat for several hours, producing the 3-methyl-1,4-naphthalenedione derivatives 12.

3-Hydroxy analogs may be produced by substituting 2,3-epoxy-2,3-dihydro-1,4-naphthoquinone in the reaction scheme for Flowchart V.

The novel compounds of the present invention are highly active as antiasthmatic and antiallergic agents as will be demonstrated hereinbelow.

The bronchospasm of allergic asthma is a consequence of the release of mediators, such as histamine and slow-reacting substances from mast cells. The role of mediator release in the induction of an asthmatic attack has been fully reviewed and documented, see Kaliner, M. and Austen, K. F., Bronchial Asthma Mechanisms and Therapeutics, E. B. Weiss, Editor, Little, Brown and Company, Boston, 163 (1976); Lichtenstein, L. M., Asthmaphysiology, Immunopharmacology and Treatment, Second International Symposium, L. M. Lichtenstein and K. F. Austen, Editors, Academic Press, New York, 51 (1979); and Bell, S. C., et al., Annual Reports in Medicinal Chemistry, 14, 51, H. J. Hess, Editor, Academic Press, New York (1979).

The novel compounds of this invention have been tested by the procedure of Lichtenstein, L. M. and Osler, A. G., J. Exp. Med., 120, 507–530 (1964), which evaluates the ability of compounds to inhibit mediator (histamine) release from immunologically stimulated human basophils.

Reagents

10X Concentrated Tris Buffer

Dissolve 140.3 g of sodium chloride, 7.45 g of potassium chloride and 74.5 g of Trizma-Tris Pre-Set, Reagent Grade, pH 7.6, at 25° C. (Sigma Chemical Co.) in sufficient water to give a final volume of 2 liters.

Human Albumin (Sigma Chemical Co.) (30 mg/ml)

Calcium and Magnesium Stocks

Made to 0.075M and 0.5M respectively, with calcium chloride dihydrate and magnesium chloride hexahydrate.

Tris-A Buffer

A 10 ml portion of 10X Tris Buffer and 1.0 ml of human albumin are diluted to 100 ml with water.

Tris ACM Buffer

A 10 ml portion of 10X Tris Buffer, 1.0 ml of human albumin, 0.8 ml of calcium stock and 0.2 ml of magnesium stock are diluted to 100 ml with water.

Rabbit Antihuman IgE

Behring Diagnostics (Generally used at 10 $\mu$g protein/ml final concentration.)

House Dust Mite Extract (Dermatophagoides Farinae)

Strength 1:100 (w:v) allergenic extract, Hollister-Stier Labs. Generally this is diluted 1:1000 to 1:10,000 (considering the vial as stock).

Other Allergens

Intradermal solutions or intramuscular preparations for hyposensitization, Hollister-Stier Labs. The final concentration used is on the order of 1 PNU/ml.

Separation of Leukocytes from Human Blood and Challenge

Eighty milliliters of blood is withdrawn from subjects with known histamine release to anti-IgE, ragweed antigen or other specific allergen, using four 20 ml heparinized tubes. This 80 ml of blood is mixed with 20 ml of saline containing 0.6 g of dextrose and 1.2 g of dextran. The blood is allowed to sediment at room temperature in two 50 ml polycarbonate centrifuge tubes until a sharp interface develops between the red cells and plasma (60–90 minutes). The plasma (top) layer from each tube is withdrawn by pipet and transferred to respective 50 ml polycarbonate tubes. The plasma is centrifuged for 8 minutes at 110×G at 4° C. The supernatant is carefully poured off as completely as possible and the cell button is resuspended in 2–3 ml of Tris-A buffer using a siliconized Pasteur pipet. The resuspension is accomplished by drawing the liquid gently in an out of the pipet, with the tip below the liquid, until an even suspension of cells is obtained. Sufficient Tris-A buffer is then added to bring the volume in the tube to about 45 ml and the tube is centrifuged at 110×G for 8 minutes at 4° C. The supernatant is poured off and the cell button is resuspended and centrifuged as described above. The supernatant is poured off and the cell button suspended in 2–3 ml of Tris-ACM buffer to make the final volume sufficient to allow addition to the reaction tubes.

Reaction tubes containing anti-IgE or antigens, either alone or with test compound in a total volume of 0.2 ml are prepared and placed in a 37° C. bath. The cells are warmed to 37° C. and frequently swirled to ensure an even suspension, while 1.0 ml aliquots are added to each reaction tube. The tubes are then incubated for 60 minutes at 37° C., vortexing the tubes gently every 15 minutes to keep the cells evenly suspended. When the reaction is complete, the tubes are centrifuged at 4° C. for 10 minutes at 1500 rpm to sediment the cells. One ml aliquots of supernatant are transferred to 12 mm by 75 mm polyethylene tubes and 0.2 ml of 8% perchloric acid is added to each tube. Blanks and totals are included in each test. The blanks have cells and all reagents except antigen or anti-IgE. The totals contain 0.24 ml of 8% perchloric acid, one ml of cells and 0.2 ml of buffer. All samples are then centrifuged to remove the precipitate protein.

Assay of Released Histamine by the Automated Fluorometric Method

This automated method has been described by Siraganian, R. P., in Anal. Biochem., 57, 383 (1974) and J. Immunol. Methods, 7, 283 (1975) and is based on the manual method of Shore, P. A., et al., J. Pharmacol. Exp. Ther., 217, 182 (1959).

The automated system consists of the following Technicon Autoanalyzer II components: Sampler IV, Dual-Speed Proportioning Pump III, Fluoronephelometer with a narrow pass primary filter 7-60 and a secondary filter 3-74, Recorder, and Digital Printer. The manifold used is the one described by Siraganian vide supra, with the following modifications: the dialyzer is omitted; all pumping tubes pass through a single proportioning pump with large capacity and twice the volume of sample is taken for analysis.

The automated chemistry consists of the following steps: Extraction from alkaline saline into butanol, back extraction into dilute hydrochloric acid by addition of heptane, reaction of histamine with o-phthaldialdehyde (OPT) at high pH and conversion of the OPT adduct to a stable fluorophore with phosphoric acid. The reaction product is then passed through the fluorometer. The full scale response is adjusted to 50 ng histamine base with a threshold sensitivity of approximately 0.5 ng.

Calculation of the Results of Histamine Release Tests

The instrument blank (wash) is substracted from the ng histamine of each sample. Then the ng histamine of each sample is divided by the mean of the three totals (cells lysed with perchloric acid) to obtain percent release.

Control samples contain antigen but no test compound. Blank (or spontaneous release) samples contain neither antigen nor test compound. The mean of the blanks (three replicates) is substracted from the percent release for controls and test compounds.

The means for control and test compound groups are computed and the result for a test compound is computed as percent of control by the formula:

100×% Histamine Release with Test compound/ % Histamine Release in Controls

Values obtained at different concentrations of test compound are used to calculate an $ED_{50}$ (the concentration in $\mu M$ which causes a 50% inhibition of histamine release) by linear regression. A compound is considered active if the $ED_{50}$ is $\leq 48$ $\mu M$.

The results of this test on typical compounds of this invention appear in Table I.

TABLE I

Inhibition of Histamine Release from Immunologically Stimulated Human Basophils

| Compound | $ED_{50}$ $\mu M$ |
|---|---|
| 4-(3-chloro-1,4-dioxo-2-naphthyl)-1-piperazine-carboxylic acid, ethyl ester | 5.5 |
| 2-chloro-3-[methyl[2-[methyl(phenylmethyl)amino]-ethyl]amino]-1,4-naphthalenedione, hydrochloride | 4.0 |
| 2-chloro-3-[4-(phenylmethyl)-1-piperazinyl]-1,4-naphthalenedione | 10.4 |
| 4-[[4-(3-chloro-1,4-dihydro-1,4-dioxo-2-naphthalenyl)-1-piperazinyl]acetyl]morpholine | 20.6 |
| 1-[[4-(3-chloro-1,4-dihydro-1,4-dioxo-2-naphthalenyl)-1-piperazinyl]acetyl]pyrrolidine | 14.9 |
| 2-chloro-3-[4-(2-pyridinyl)-1-piperazinyl]-1,4-naphthalenedione, hydrochloride | 4.6 |
| 2-[[2-(2-benzothiazolylmethylamino)ethyl]methyl-amino]-3-chloro-1,4-naphthalenedione | 6.4 |
| 2-chloro-3-[4-(phenylmethyl)-1-piperazinyl]-1,4-naphthalenedione, hydrochloride | 13.4 |
| 2-[4-(2-benzothiazolyl)-1-piperazinyl]-3-chloro-1,4-naphthalenedione, hydrochloride | 5.4 |
| 4-(3-chloro-1,4-dihydro-1,4-dioxo-2-naphthalenyl)-1-piperazinecarboxylic acid, ethyl ester, hydrochloride | 1.5 |
| 2-chloro-3-(3-methyl-1-piperazinyl)-1,4-naphthalenedione | 3.0 |
| 4-(3-chloro-1,4-dihydro-1,4-dioxo-2-naphthalenyl)-1-piperazinecarboxylic acid, 2-methylpropyl ester | 16.5 |
| 1-(2-chlorobenzoyl)-4-(3-chloro-1,4-dihydro-1,4-dioxo-2-naphthalenyl)piperazine | 1.8 |

The ability of these compounds to inhibit lipoxygenase activity in terms of the suppression of the release and biosynthesis of leukotriene B4 (LTB4) and 5-hydroxy-eicosatetraenoic acid (5-HETE) was measured as follows.

In this assay $3 \times 10^7$ peritoneal neutrophils derived from guinea pigs were incubated at 37° C. in Dulbeccos buffer containing 50 mM tris buffer (pH 7.4). Five minutes before the addition of 100 $\mu M$ arachidonic acid and 20 $\mu M$ calcium ionophore (A23187), control vehicle or the test compounds were added to the neutrophils at a concentration of 10 $\mu g/ml$.

Three minutes after the addition of arachidonic acid and calcium ionophore the total lipid was partitioned into chloroform after adjusting the pH to 3 with citric acid and the addition of equal parts of methanol and chloroform.

The 5-HETE and LTB4 were resolved by HPLC using a 5 $\mu M$, 4×25 cm octadecyl silica column (IBM Instruments) with 70–80% methanol in water adjusted to pH 3.0 with acetic acid. As the mobile phase was pumped at 1.0 ml/-minute, LTB4 and 5-HETE were detected by absorbance at 270 and 236 nm, respectively.

LTB4 and 5-HETE were quantitated by comparison with the control and the results were expressed as a percent of control. The lower the percentage, the more active the compound.

The results of this test on representative compounds of this invention appear in Table II.

TABLE II

Inhibition of Neutrophil Lipoxygenase from Immunologically Stimulated Guinea Pig Neutrophiles

| Compound | % of Control | |
|---|---|---|
|  | LTB4 | 5-HETE |
| 4-(3-chloro-1,4-dioxo-2-naphthyl)-1-piperazinecarboxylic acid, ethyl ester | 0 | 0 |
| 2-chloro-3-[4-(phenylmethyl)-1-piperazinyl]-1,4-naphthalenedione | 0 | 0 |
| 2-chloro-3-[4-(2-quinolinyl)-1-piperazinyl]-1,4-naphthalenedione, hydrochloride | 0 | 0 |
| 4-(3-chloro-1,4-dihydro-1,4-dioxo-2-naphthalenyl)N—(2-chlorophenyl)-1-piperazinecarboxamide | 22.2 | 19.9 |
| 4-(3-chloro-1,4-dihydro-1,4-dioxo-2-naphthalenyl)-N—(2-fluorophenyl)-1-piperazinecarboxamide | 0 | 2.0 |
| 2-[4-(1,3-benzodioxol-5-ylmethyl)-1-piperazinyl]-3-chloro-1,4-naphthalenedione, hydrochloride | 0 | 0 |
| 4-(3-chloro-1,4-dihydro-1,4-dioxo-2-naphthalenyl)-N—[3-(trifluoromethyl)phenyl]-1-piperazinecarboxamide | —* | 0 |
| N—[3-[4-(2-benzothiazolyl)-1-piperazinyl]-1,4-dihydro-1,4-dioxo-2-naphthalenyl]-acetamide | 0 | 0 |
| 4-(3-chloro-1,4-dihydro-1,4-dioxo-2-naphthalenyl)-N—(4-chlorophenyl)-1-piperazinecarboxamide | — | 1.4 |
| 2-chloro-3-[4-(2-pyridinyl)-1-piperazinyl]-1,4-naphthalenedione, hydrochloride | 6.1 | 1.3 |
| 2-[[2-(2-benzothiazolylmethylamino)ethyl]-methylamino]-3-chloro-1,4-napthalenedione | 0 | 0.2 |
| 2-[4-(2-benzothiazolyl)hexahydro-1H-1,4-diazepin-1-yl]-3-chloro-1,4-naphthalenedione | — | 1.1 |
| 2-chloro-3-[4-(2-pyrimidinyl)-1-piperazinyl]-1,4-naphthalenedione | — | 34.3 |
| 4-(1,4-dihydro-3-methyl-1,4-dioxo-2-naphthalenyl)-1-piperazinecarboxylic acid, ethyl ester | — | 2.2 |
| 2-[4-(2-benzothiazolyl)-1-piperazinyl]-3-methyl-1,4-naphthalenedione | 20.8 | 0.8 |
| 2-methyl-3-[4-(phenylmethyl)-1-piperazinyl]-1,4-naphthalenedione | 4.8 | 0.7 |
| 2-methyl-3-[4-[3-(trifluoromethyl)phenyl]-1-piperazinyl]-1,4-naphthalenedione | — | 0 |
| N—[1,4-dihydro-1,4-dioxo-3-[4-[3-(trifluoromethyl)phenyl]-1-piperazinyl]-2-naphthalenyl]acetamide | — | 0.3 |
| 2-methyl-3-[4-(2-pyridinyl)-1-piperazinyl]-1,4-naphthalenedione | 0 | 0 |
| N—(4-chlorophenyl)-4-(1,4-dihydro-3-methyl-1,4-dioxo-2-naphthalenyl)-1-piperazinecarboxamide | — | 8.8 |
| 2-[4-(2-benzoxazolyl)-1-piperazinyl]-3-chloro-1,4-naphthalenedione | 13.5 | 19.6 |
| 2-chloro-3-[4-(phenylmethyl)-1-piperazinyl]-1,4-naphthalenedione, hydrochloride | 28.3 | 35.6 |
| 2-[4-(2-benzothiazolyl)-1-piperazinyl]-3-chloro-1,4-naphthalenedione, hydrochloride | 32.6 | 23.1 |
| 4-(3-chloro-1,4-dihydro-1,4-dioxo-2-naphthalenyl)-1-piperazinecarboxylic acid, ethyl ester, hydrochloride | 9.3 | 6.9 |
| 4-(3-chloro-1,4-dihydro-1,4-dioxo-2-naphthalenyl)-N—(3-chlorophenyl)-2-methyl-1-piperazinecarboxamide | 15.2 | 25.7 |
| 4-(3-chloro-1,4-dihydro-1,4-dioxo-2-naphthalenyl)-1-piperazinecarboxylic acid, 2-methylpropyl ester | 27.4 | 31.6 |
| 1-(4-butylbenzoyl)-4-(3-chloro-1,4-dihydro- | 23.2 | 13.7 |

TABLE II-continued

Inhibition of Neutrophil Lipoxygenase from
Immunologically Stimulated Guinea Pig Neutrophiles

| Compound | % of Control | |
|---|---|---|
| | LTB4 | 5-HETE |
| 1,4-dioxo-2-naphthalenyl)piperazine | | |

*Dashes in the LTB4 column represent no measurement because of assay interference.

An in vivo test used to establish anti-asthma activity for the compounds of the present invention is the mouse passive cutaneous anaphylaxis (PCA) test described as follows.

Preparation of Immunoglobulin E (IGE) and G (IGG)

Female $B_6XD_2F1$ mice (Jackson Laboratories) are given an intraperitoneal injection of 0.5 ml of saline with 1 mcg of DNP-ovalbumin and 1 mg of aluminum hydroxide gel (Wyeth Amphojel®). One and two months later the mice are boosted with the same antigen preparation. One week after the second boost the mice are sacrificed and the serum collected. The sera are pooled and titered to obtain a 48 hour PCA lesion slightly greater than 1 cm in diameter.

Passive Anaphylaxis Test

At −50 hours (relative to antigen challenge at 0 time) 50 microliters of IGE or IGG is injected intradermally on the side of the mouse posterior to the axilla at the level of the diaphragm. At this point the mice are placed in individual numbered cages and randomly assigned to control and/or treatment groups (typically 15 mice in the control group with 10 in each treatment group). Challenge and reading are performed in serial order so that reading of the assay is essentially blind. At −1 hour the control animals receive an IP injection of 0.5 ml of a 0.05% solution of carboxymethylcellulose in saline. For drug treated animals the drug is dissolved or suspended in a 0.1% carboxymethylcellulose solution (total volume 0.5 ml) and administered orally at −1 hour. At 0 time the mice are anesthetized with ether and 0.5 ml of saline containing 0.1 mg of dinitrophenylated (DNP)-ovalbumin and 2.5 mg Evans blue dye is injected into the tail vein. At +15 minutes the mice are sacrificed by cervical dislocation, the dorsal skin removed, and the blue PCA spots are examined on the inside surface. The largest and smallest diameters of the lesion and a qualitative estimate of intensity of color are recorded. The mean of the products of diameters (area) for mice in a given treatment group are compared with the control group. If the area for a treatment group is significantly smaller than the lesion area for the control group (p <0.05 for two-tailed student's t-test) the test compound is considered active as an anti-asthmatic agent. Results for typical compounds of this invention when tested as described above appear in Table III, wherein the inhibitory dose ($ID_{50}$) estimated to inhibit the size of lesions in 50% of the animals relative to control is given.

TABLE III

Mouse Passive Cutaneous Anaphylaxis Test

| Compound | $ID_{50} \mu M$ | |
|---|---|---|
| | IGE | IGG |
| 4-(3-chloro-1,4-dioxo-2-naphthyl)-1-piperazinecarboxylic acid, ethyl ester | 61.0 | 16.0 |
| 2-chloro-3-[methyl[2-methyl(phenylmethyl)-amino]ethyl[amino]-1,4-naphthalenedione, hydrochloride | 30.3 | 41.2 |

TABLE III-continued

Mouse Passive Cutaneous Anaphylaxis Test

| Compound | $ID_{50} \mu M$ | |
|---|---|---|
| | IGE | IGG |
| 2-chloro-3-[4-(phenylmethyl)-1-piperazinyl]-1,4-naphthalenedione | 25.0 | 50.0 |
| 1-[[4-(3-chloro-1,4-dihydro-1,4-dioxo-2-naphthalenyl)-1-piperazinyl]acetyl]pyrrolidine | 25.0 | 25.0 |
| 4-(3-chloro-1,4-dihydro-1,4-dioxo-2-naphthalenyl)-1-piperazinecarboxylic acid, ethyl ester, hydrochloride | 25.0 | 25.0 |

The novel compounds of the present invention are effective as antiasthmatic agents in mammals when administered in amounts ranging from about 0.1 mg to about 100 mg/kg of body weight per day. A preferred dosage regimen for optimum results would be from about 0.1 mg to about 25 mg/kg of body weight per day, and such dosage units are employed that a total of from about 7 mg to about 1.8 g of the active compound for a subject of about 70 kg of body weight are administered in a 24 hour period. This dosage regimen may be adjusted to provide the optimum thereapeutic response. For example, several divided doses may be administered daily or the dose may be proportionally reduced as indicated by the exigencies of the therapeutic situation. A decided practical advantage is that these active compounds may be administered in any convenient manner such as by the oral, aerosol, intravenous, intramuscular, or subcutaneous routes.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, these active compounds may be incorporated with excipients and used in the form of ingestible tablets, buccal tablets, troches, capsules, elixirs, suspensions, syrups, wafers, suppositories and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as pepermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although various mixtures of the aforementioned non-volatile polyethylene glycols may be employed, it is preferred to use a mixture having an average molecular weight of from about 200 to about 400.

In addition to the active compound, the parenteral solutions may contain various preservatives which may be used to prevent bacterial and fungal contamination. Such preservatives are, for example, myristyl-gamma picolinium chloride, phenyl mercuric nitrate, benzalkonium chloride, phenethyl alcohol, p-chlorophenyl-alpha-glycerol ether, methyl and propyl parabens and thimerosal. As a practical matter, it is also convenient to employ antioxidants. Suitable antioxidants include, for example, sodium bisulfite, sodium metabisulfite and sodium formaldehyde sulfoxylate. Generally, from about 0.05% to about 0.2% concentrations of antioxidant are employed. These compounds may also be administered by inhalation using conventional Aerosol ® formulations.

The invention will be described in greater detail in conjunction with the following specific examples.

Example 1

4-(3-Chloro-1, 4-dioxo-2-naphthyl)-1-piperazinecarboxylic acid, ethyl ester

A mixture of 11.35 g of 2,3-dichloro-1,4-naohthoquinone, 15.8 g of 1-piperazinecarboxylic acid, ethyl ester and 400 ml of absolute ethanol was heated at reflux for 3 hours and then evaporated to dryness. The residue was taken up in 300 ml of dichloromethane and filtered through silica gel. The filtrate was evaporated and the residue triturated with ether, giving 8.0 g of the desired product as red crystals, mp 120°–122° C.

Example 2

2-Chloro-3-[methyl[2-[methyl(phenylmethyl) amino]-ethyl]amino]-1,4-naphthalenedione, hydrochloride A 4.5 g portion of methyl 2-[methyl (phenylmethyl)-amino]ethylamine was added to a stirred slurry of 5.6 g of 2,3-dichloro-1,4-naphthoquinone in 150 ml of absolute ethanol. Stirring was continued for 16 hours, then the mixture was heated at reflux for one hour and filtered while hot. The mixture was then cooled at −10° C. and filtered. This filtrate was diluted with 100 ml of ether and cooled at −10° C. The resulting precipitate was collected, washed with ether and dried in vacuo at 100° C., giving 3.5 g of the desired product as orange crystals, mp 188°–190° C. (dec.).

Following the procedure of Examples 1 and 2, using appropriate amine starting materials and 2, 3-dichloro-1,4-naphthoquinone the products of Examples 3–19, listed in Table IV were obtained.

TABLE IV

| Ex. | Amine | Product | MP °C. |
|---|---|---|---|
| 3 | N—[3-(trifluoromethyl)-phenyl]piperazine | 2-chloro-3-[4-[3-(trifluoromethyl)phenyl]-1-piperazinyl]-1,4-naphthalenedione | 124–126 |
| 4 | N—(p-chlorobenzhydryl)-piperazine | 2-chloro-3-[4-[(4-chlorophenyl)phenylmethyl]-1-piperazinyl]-1,4-naphthalenedione | 158–161 |
| 5 | N—benzylpiperazine | 2-chloro-3-[4-(phenylmethyl)-1-piperazinyl]-1,4-naphthalenedione | oil |
| 6 | N—acetylmorpholino piperazine | 4-[[4-(3-chloro-1,4-dihydro-1,4-dioxo-2-naphthalenyl)-1-piperazinyl]acetyl]morpholine | 159–161 |
| 7 | N—acetylpyrrolidino piperazine | 1-[[4-(3-chloro-1,4-dihydro-1,4-dioxo-2-naphthalenyl)-1-piperazinyl]acetyl]pyrrolidine | 110–113 |
| 8 | N—(2-pyridinyl)piperazine | 2-chloro-3-[4-(2-pyridinyl)-1-piperazinyl]-1,4-naphthalenedione, hydrochloride | oil |
| 9 | N—benzothiazolylmethyl-aminoethyl methylamine | 2-[[2-(2-benzothiazolylmethylamino)ethyl]methyl-amino]-3-chloro-1,4-naphthalenedione | oil |
| 10 | N—(2-quinolinyl)piperazine | 2-chloro-3-[4-(2-quinolinyl)-1-piperazinyl]-1,4-naphthalenedione, hydrochloride | >100 |
| 11 | N—(1,3-benzodioxol-5-yl-methyl)piperazine | 2-[4-(1,3-benzodioxol-5-ylmethyl)-1-piperazinyl]-3-chloro-1,4-naphthalenedione, hydrochloride | >200 |
| 12 | N—(2-pyrimidinyl)piperazine | 2-chloro-3-[4-(2-pyrimidinyl)-1-piperazinyl]-1,4-naphthalenedione | 136–137 |
| 13 | piperazinecarboxaldehyde | 4-(3-chloro-1,4-dihydro-1,4-dioxo-2-naphthalenyl)-1-piperazinecarboxaldehyde | 182–183 |
| 14 | 2-methylpiperazine | 2-chloro-3-(3-methyl-1-piperazinyl)-1,4-naphthalenedione | 134–136 |
| 15 | N—benzylpiperazine | 2-chloro-3-[4-(phenylmethyl)-1-piperazinyl]-1,4-napthalenedione, hydrochloride | 117–119 |
| 16 | piperazinecarboxylic acid ethyl ester | 4-(3-chloro-1,4-dihydro-1,4-dioxo-2-naphthalenyl)-1-piperazinecarboxylic acid, ethyl ester, hydrochloride | 107–108 |
| 17 | N—(2-benzothiazolyl)-1-piperazine | 2-[4-(2-benzothiazolyl)-1-piperazinyl]-3-chloro-1,4-naphthalendione, hydrochloride | 141–146 |
| 18 | N—(6-chloro-3-pyridazin-yl)-1-piperazine | 2-chloro-3-[4-(6-chloro-3-pyridazinyl)-1-piperazinyl]-1,4-naphthalenedione, hydrochloride | 140–142 |
| 19 | N—[2-(3-bromophenyl)-4- | 2-[4-[2-(3-bromophenyl)-4-pyrimidinyl]-1-pipera- | 185–187 |

TABLE IV-continued

| Ex. | Amine | Product | MP °C. |
|---|---|---|---|
| | pyrimidinyl]-1-piperazine | zinyl]-3-chloro-1,4-naphthalenedione | |

Example 20

N-[1,4-Dihydro-1,4-dioxo-3-[4-(phenylmethyl)-1-piperazinyl]-2-naphthalenyl]acetamide A mixture of 500 mg of 2-acetylamino-3chloro-1,4-naphthoquinone, 800 mg of N-benzylpiperazine and 40 ml of absolute ethanol was heated at reflux for 3 hours, then the solvent was removed. The remainder was passed through a small plug of silica gel and eluted with chloroform. The eluate was concentrated to a solid which was recrystallized from dichloromethane/hexane, giving 700 mg of the desired product, mp 153°–155° C.

Following the procedure of Example 20, using appropriate amine starting materials and 2-acetylamino-3-chloro-1,4-naphthoquinone, the products of Examples 21–28, listed in Table V were obtained.

TABLE V

| Ex. | Amine | Product | MP °C. |
|---|---|---|---|
| 21 | N—[2-(4-morpholinyl)-2-oxoethyl]-1-piperazine | N—[1,4-dihydro-3-[4-[2-(4-morpholinyl)-2-oxo-ethyl]-1-piperazinyl]-1,4-dioxo-2-napthalenyl]-acetamide | 190–200 |
| 22 | N—(2-oxo-2-(1-pyrrolidin-yl)ethyl]-1-piperazine | N—[1,4-dihydro-1,4-dioxo-3-[4-[2-oxo-2-(1-pyrroli-dinyl)ethyl]-1-piperazinyl]-2-naphthalenyl]-acetamide | 130–160 (dec.) |
| 23 | N—(2-benzothiazolyl)-1-piperazine | N—[3-[4-(2-benzothiazolyl)-1-piperazinyl]-1,4-dihydro-1,4-dioxo-2-naphthalenyl]acetamide | 145–150 |
| 24 | piperazinecarboxylic acid ethyl ester | 4-[3-(acetylamino)-1,4-dihydro-1,4-dioxo-2-naph-thalenyl]-1-piperazinecarboxylic acid, ethyl ester | 200–202 |
| 25 | N—(1,3-benzodioxol-5-yl-methyl)piperazine | N—[3-[4-(1,3-benzodioxol-5-ylmethyl)-1-pipera-zinyl]-1,4-dihydro-1,4-dioxo-2-naphthalenyl]-acetamide | 199–201 |
| 26 | N—(2-pyridinyl)piperazine | N—[1,4-dihydro-1,4-dioxo-3-[4-(2-pyridinyl)-1-piperazinyl]-2-naphthalenyl]acetamide | 167–169 |
| 27 | N—(4-fluorophenyl)pipera-zine | N—[3-[4-(4-fluorophenyl)-1-piperazinyl]-1,4-dihydro-1,4-dioxo-2-naphthalenyl]acetamide | 185–186 |
| 28 | N—[3-(trifluoromethyl)-phenyl]piperazine | N—[1,4-dihydro-1,4-dioxo-3-[4-[3-(trifluormeth-yl)phenyl]-1-piperazinyl]-2-naphthalenyl]acetamide | 168–170 |

Example 29

4-(3-Chloro-1,4-dihydro-1,4-dioxo-2-naphthalenyl)-N-(2-chlorophenyl)-1-piperazinecarboxamide A 2.76 g portion of 3-chloro-2piperazine-1, 4-naphthoquinone was dissolved in 75 ml of chloroform. To this was added dropwise a solution of 2-chlorophenyl isocyanate in ether. This mixture was stirred for 2 hours and then evaporated. The residue was triturated in ether, giving 2.3 g of the desired product, mp 160°–163° C.

Following the procedure of Example 29, using appropriate isocyanate starting materials and 3-chloro-2-piperazine-1,4-naphthoquinone, the products of Examples 30–32, listed in Table VI were obtained.

TABLE VI

| Ex. | Isocyanate | Product | MP °C. |
|---|---|---|---|
| 30 | 2-fluorophenyl isocyanate | 4-(3-chloro-1,4-dihydro-1,4-dioxo-2-naphthalenyl)-N—(2-fluorphenyl)-1-piperazinecarboxamide | >120 (dec.) |
| 31 | 3-(trifluoromethyl)phenyl isocyanate | 4-(3-chloro-1,4-dihydro-1,4-dioxo-2-naphthalenyl)-N—[3-(trifluoromethyl)phenyl]-1-piperazinecar-boxamide | >150 (dec.) |
| 32 | 4-chlorophenyl isocyanate | 4-(3-chloro-1,4-dihydro-1,4-dioxo-2-naphthalenyl)-N—(4-chlorophenyl)-1-piperazinecarboxamide | oil |

Example 33

4-(3-Chloro-1,4-dihydro-1,4-naphthalenyl)-1-piperazinecarboxylic acid, 2-methylpropyl ester A solution of 830 mg of 3-chloro-2-piperazinyl-1,4-naphthoquinone in 50 ml of tetrahydrofuran was added dropwise to a solution of 0.39 ml of butyl chloroformate in 10 ml of tetrahydrofuran. This mixture was stirred for 20 minutes, then filtered and the filtrate concentrated to an oil. The oil was crystallized from ether/hexane, giving 360 mg of the desired product, mp 92°–94° C.

Following the procedure of Example 33, using appropriate carbonyl chloride starting materials and 3-chloro-2-piperazinyl-1,4-naphthoquinone, the products of Examples 34–40, listed in Table VII were obtained.

TABLE VII

| Ex. | Carbonyl chloride | Product | MP °C. |
|---|---|---|---|
| 34 | 2-chlorobenzoyl chloride | 1-(2-chlorobenzoyl)-4-(3-chloro-1,4-dihydro-1,4-dioxo-2-naphthalenyl)piperazine | 97–101 |
| 35 | 4-butylbenzoyl chloride | 1-(4-butylbenzoyl)-4-(3-chloro-1,4-dihydro-1,4-dioxo-2-naphthalenyl)piperazine | oil |
| 36 | benzylchloroformate | 4-(3-chloro-1,4-dihydro-1,4-dioxo-2-naphthalenyl)-1-piperazinecarboxylic acid, phenylmethyl ester | oil |

TABLE VII-continued

| Ex. | Carbonyl chloride | Product | MP °C. |
|---|---|---|---|
| 37 | trichloroethylchloroformate | 4-(3-chloro-1,4-dihydro-1,4-dioxo-2-naphthalenyl)-1-piperazinecarboxylic acid, 2,2,2-trichloroethyl ester | oil |
| 38 | acetyl chloride | 1-acetyl-4-(3-chloro-1,4-dihydro-1,4-dioxo-2-naphthalenyl)piperazine | 135–136 |
| 39 | oleyl chloride | 1-(3-chloro-1,4-dihydro-1,4-dioxo-2-naphthalenyl)-4-(1-oxo-9-octadecenyl)piperazine | semi-solid |
| 40 | dimethylaminocarbonyl chloride | 4-(3-chloro-1,4-dihydro-1,4-dioxo-2-naphthalenyl)-N,N—dimethyl-1-piperazinecarboxamide | 113–115 |

Example 41

4-(1,4-Dihydro-3-methyl-1, 4-dioxo-2-naphthalenyl)-1-piperazinecarboxylic acid, ethyl ester A mixture of 1.88 g of 2,3-epoxy-3-methyl-1, 4-naphthoquinone, 3.16 g of piperazinecarboxylic acid, ethyl ester and 100 ml of absolute ethanol was stirred for 12 hours at 50° C. The solvent was then removed and the remainder filtered through a one inch plug of silica gel and eluted with chloroform. The eluate was evpaorated, giving 1 g of the desired product as a viscous red oil.

Following the procedure of Example 41, using appropriate amine starting materials and 2,3-epoxy-3methyl-1,4-naphthoquinone, the products of Examples 42–51, listed in Table VIII were obtained.

Example 53

N-[3-[4-(2-Benzothiazolyl)hexahydro-1H-diazepin-1-yl]-1,4-dihydro-1, 4-dioxo-2-naphthalenyl]acetamide The procedure of Example 52 was repeated, using 466 mg of N-(2-benzothiazolyl)hexahydro-1H-1, 4diazepin-1yl and 500 mg of 2acetylamino-3-chloro-1, 4-naphthoquinone, giving 400 mg of the desired product as a glass.

Example 54

N-(4-Chlorophenyl)-4-(1, 4-dihydro-3-methyl-1,4-dioxo-2naphthalenyl)-1-piperazinecarboxamide A solution of 150 mg of 3-methyl-2piperazinyl-1,4-naphthoquinone in 50 ml of tetrahydrofuran was treated with a solution of 100 mg of 4-chlorophenylisocyanate

TABLE VIII

| Ex. | Amine | Product | MP °C. |
|---|---|---|---|
| 42 | N—(2-benzothiazolyl)-1-piperazine | 2-[4-(2-benzothiazolyl)-1-piperazinyl]-3-methyl-1,4-naphthalenedione | 100–150 (dec.) |
| 43 | N—benzylpiperazine | 2-methyl-3-[4-(phenylmethyl)-1-piperazinyl]-1,4-naphthalenedione | 101–103 |
| 44 | N—(2-pyridinyl)piperazine | 2-methyl-3-[4-(2-pyridinyl)-1-piperazinyl]-1,4-naphthalenedione | 87–92 |
| 45 | N—[3-(trifluoromethyl)-phenyl]piperazine | 2-methyl-3-[4-[3-(trifluoromethyl)phenyl]-1-piperazinyl]-1,4-naphthalenedione | 109–110 |
| 46 | N—acetylmorpholino piperazine | 4-[[4-(1,4-dihydro-3-methyl-1,4-dioxo-2-naphthalenyl)-1-piperazinyl]acetyl]morpholine | semi-solid |
| 47 | N—acetylpyrrolidino piperazine | 1-[[4-(1,4-dihydro-3-methyl-1,4-dioxo-2-naphthalenyl)-1-piperazinyl]acetyl]pyrrolidine | semi-solid |
| 48 | piperazinecarboxaldehyde | 4-(1,4-dihydro-3-methyl-1,4-dioxo-2-naphthalenyl)-1-piperazinecarboxaldehyde | 143–145 |
| 49 | N—(4-fluorophenyl)piperazine | 2-[4-(4-fluorophenyl)-1-piperazinyl]-3-methyl-1,4-naphthalenedione | 120–121 |
| 50 | N—(1,3-benzodioxol-5-ylmethyl)piperazine | 2-[4-(1,3-benzodioxol-5-ylmethyl)-1-piperazinyl]-3-methyl-1,4-naphthalenedione | 90–91 |
| 51 | N—phenylpiperazine | 2-methyl-3-(4-phenyl-1-piperazinyl)-1,4-naphthalenedione | 59–61 |

Example 52

2-[4-(2-Benzothiazolyl)hexahydro-1H-diazepin-1-yl]b 3-chloro-1,4-naphthalenedione A 2.33 g portion of N-(2-benzothiazolyl) hexahydro-1H-1,4-diazepin-1-yl was dissolvedom 25 of absolute ethanol and 1.13 g of 2,3-dichloro-1, 4-naphthoquinone was added. This mixture was heated at reflux for 4 hours, then cooled to room temperature and the solvent removed. The remainder was filtered through a plug of silica gel and then eluted with chloroform followed by 5% methanol in chloroform. The eluate was concentrated to a solid which was triturated with ether, giving 400 mg of the desired product as a glass.

in 10 ml of tetrahydrofuran. This mixture was stirred ½ hour, then evaporated in vacuo and the residue taken up in dichloromethane and filtered. The filtrate was evaporated and the residue recrystallized from dichloromethane/hexane, giving 200 mg of the desired product, mp 190°–192° C.

Example 55

2-[4-(2-Benzoxazolyl)-1-piperazinyl]-3-chloro-1,4-naphthalenedione

A solution of 1.0 g of N-(2-benzoxazolyl)-1piperazine and 0.82 g of diazobicycloundecane in 50 ml of toluene was prepared. A 1.11 g portion of 2, 3-dichloro-1,4-naphthoquinone was added and the mixture was stirred for 12 hours and then evaporated. The residue was taken up in dichloromethane, filtered and the filtrate

Example 56

1-(3-chloro-1,4-dihydro-1,4-dioxo-2-naphthalenyl)-4-[(2-chlorophenyl)sulfonyl]piperazine A solution of 1.0 g of 3-chloro-2-piperazinyl-1,4-naphthoquinone in 20 ml of pyridine was prepared. To this was added 750 mg of 2-chlorobenzenesulfonyl chloride. The mixture was stirred for 10 minutes, then heated on a steam bath for 2 hours, then diluted with water and extracted with three 50 ml portions of dichloromethane. The extracts were combined, washed with water, dried and evaporated in vacuo. The residue was chromatographed on silica gel, eluting with 2% methanol in chloroform. The active fraction was evaporated in vacuo, giving 830 mg of the desired product, mp 176°–177° C.

Example 57

1-(3-Chloro-1,4-dihydro-1,4-dioxo-2-naphthalenyl)-4-[[2-(trifluoromethyl)phenyl]sulfonyl]piperazine A 1.5 g portion of 3-chloro-2-piperazinyl-1,4-naphthoquinone and 1.26 g of 2-trifluoromethylbenzenesulfonyl chloride were reacted as described in Example 56, giving 1.53 g of the desired product, mp 122°–124° C.

Example 58

4-(3-Chloro-1,4-dihydro-1,4-dioxo-2-naphthalenyl)-N-(3-chlorophenyl)-2-methyl-1-piperazinecarboxamide A solution of 1.0 g of 2-chloro-3-(3-methyl-1piperazinyl)-1,4-naphthalenedione in 300 ml of ether was prepared. A solution of 530 mg of 3-chlorophenyl isocyanate in 25 ml of ether was added, the mixture was stirred for ½ hour, then evaporated in vacuo. The residue was dissolved in dichloromethane, filtered and the filtrate evaporated, giving 950 mg of the desired product, mp 112°–114° C.

Example 59

N-Acetyl-N-[3-[4-(4-fluorophenyl)-1-piperazinyl]-1,4-dihydro-1,4-dioxo-2-naphthalenyl]acetamide A mixture of 1.66 g of 2-[N,N-diacetylamino]-3-chloro-1,4-naphthoquinone and 1.441 g of 1-(4-fluorophenyl)-piperazine in 50 ml of ethanol was refluxed overnight, then evaporated in vacuo. The residue was dissolved in dichloromethane, filtered through silica gel and eluted with chloroform:methanol (100:2). The eluent was evaporated and the residue crystallized from dichloromethane/-hexane, giving 800 ml of the desired product, mp 149°–150° C.

Example 60

N-Acetyl-N-[1,4-dihydro-1,4-dioxo-3-[4-[(1,2,3,6-tetrahydro-2,6-dioxo-4-pyrimidinyl) methyl]-1-piperazinyl]-2-naphthalenyl]acetamide A 1.166 g portion of 2-[N,N-diacetylamino]-3-chloro-1,4-naphthoquinone and 1.681 g of 6-methyluracil-1-piperazine were reacted as described in Example 59, giving 960 mg of the desired product, mp 152°–154° C.

Example 61

2-Hydroxy-3-[4-[3-(trifluoromethyl) phenyl]-1-piperazinyl]-1,4-naphthalenedione

A mixture of 1.74 g of 2,3-epoxy-2,3-dihydro-1,4-naphthoquinone and 2.30 g of N-[3-(trifluoromethyl) phenyl]-piperazine in 100 ml of absolute ethanol was stirred for 20 hours, then evaporated. The residue was dissolved in dichloromethane, filtered through hydrous magnesium silicate and then chromatographed on silica gel, eluting with hexane:ethyl acetate (4:1), giving 1.2 g of the desired product, mp 167°–169° C.

Example 62

2-Hydroxy-3-[methyl[2-[methyl (phenylmethyl)amino]-ethyl]amino]-1,4-naphthalenedione A mixture of 2.61 g of 2,3-epoxy-2, 3-dihydro-1,4-naphthoquinone, 2.67 g of N-benzyl-N,N'-dimethylethylene-diamine and 150 ml of absolute ethanol was stirred for 20 hours, then concentrated to one-half its original volume and refrigerated overnight. The solvent was removed, the residue dissolved in dichloromethane and passed through a pad of hydrous magnesium silicate and silica, eluting first with dichloromethane, then with 1% methanol in dichloromethane. The active fraction was flash chromatographed eluting with dichloromethane followed by 2% methanol in dichloromethane. The active fraction was evaporated and the residue triturated in dichloromethane/-hexane giving 900 mg of the desired product, mp 121°–123° C.

Example 63

4-(1,4-Dihydro-3-hydroxy-1,4-dioxo-2-naphthalenyl)-1-piperazinecarboxaldehyde

A mixture of 3.48 g of 2,3-epoxy-2,3-dihydro-1,4-naphthoquinone, 2.28 of 1-piperazinecarboxaldehyde and 200 ml of absolute ethanol was stirred for 20 hours, then concentrated to one-half its original volume and refrigerated overnight. The solid was collected and recrystallized from dichloromethane/ethanol, giving 2.65 g of the desired product, mp 200°–203° C.

Example 64

2-[4-(2-Benzoxazolyl)-1-piperazinyl]-3-hydroxy-1,4-naphthalenedione

A mixture of 3.48 g of 2,3-epoxy-2, 3-dihydro-1,4-naphthoquinone, 2.03 g of 2-(1-piperazinyl)benzoxazole and 200 ml of absolute ethanol was stirred for 18 hours and then filtered. The filtrate was concentrated to dryness and the residue flash chromatographed, eluting with dichloromethane, then 1% methanol in dichloromethane. The desired fraction was evaporated, then recrystallized twice from dichloromethane/ethanol, giving 533 mg of the desired product, mp 190° C. (dec.).

Example 65

4-(1,4-Dihydro-3-hydroxy-1,4-dioxo-2-naphthalenyl)-1-piperazinecarboxylic acid, ethyl ester A mixture of 1.174 g of 2,3-epoxy-2, 3-dihydro-1,4-naphthoquinone, 1.58 g of ethyl-N-piperazinocarboxylate and 100 ml of absolute ethanol was stirred for 24 hours, then evaporated. The residue was chromatographed on silica gel, eluting with 5% methanol in chloroform, giving 1.0 g of the desired product, mp 115°–118° C.

Example 66

2-[4-[2-(3-Bromophenyl)-4-pyrimidinyl]-1-piperazinyl]-3-methyl-1,4-naphthalenedione A mixture of 940 mg of 2,3-epoxy-2-methyl-1,4-naphthoquinone, 1.59 g of 3-bromophenyl-4-pyrimidinyl-1-piperazine and absolute ethanol was stirred for 48 hours. The solid was collected, washed with absolute ethanol and dried, giving 500 mg of the desired product, mp 120° C. (dec.).

We claim:

1. A compound selected from the group consisting of those of the formula:

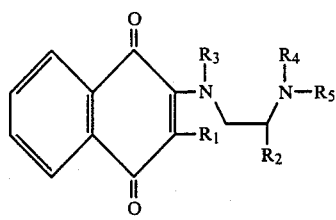

wherein $R_1$ is selected from the group consisting of halogen, hydroxy, alkyl($C_1$-$C_4$), alkoxy($C_1$-$C_3$), —NHCOCH$_3$ and —N(ClCG$_3$)$_2$; $R_2$ is seleccted from the group hydrogen and alkyl($C_1$-$C_4$); $R_3$ and $R_4$ are individually alkyl($C_1$-$C_3$); $R_5$ is selected from the group consisting of hydrogen, formyl, acetyl, —COOalkyl($C_1$-$C_4$), —COOCH$_2$C(halogen)$_3$, —CO(CH$_2$)$_7$CH=CH(CH$_2$)$_7$CH$_3$, —CON[alkyl($C_1$—$C_3$)]$_2$, phenyl, benzyl, 2-, 3- or 4-halobenzoyl, 2-,3- or 4-alkyl($C_1$-$C_6$)benzoyl, monosubstituted phenyl (wherein the substituents may be ortho, meta or para and are halogen or trifluoromethyl), monosubstituted phenyl carboxamide (wherein the substituents may be meta or para and are halogen or trifluoromethyl) and moieties of the formulae:

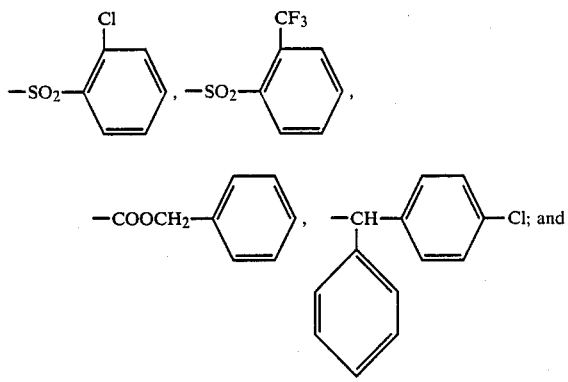

the pharmacologically acceptable acid-addition salts thereof.

2. The compound according to claim 1; 2-chloro-3-[methyl[2-[methyl(phenylmethyl)amino]ethyl]amino]-1,4-naphthalenedione.

3. The compound according to claim 1; 2-hydroxy-3-[methyl]2-[methyl(phenylmethyl)amino]ethyl]amino]-1,4-naphthalenedione.

4. A method of treating asthma and allergic diseases in a warm-blooded animal which comprises administering to said animal an effective amount of a compound of claim 1.

5. A method of treating inflammation in a warm-blooded animal which comprises administering to said animal an effective amount of a compound of claim 1.

6. A composition of matter in dosage unit form comprising from about 5 mg to about 1500 mg of a compound of claim 1.

* * * * *